United States Patent [19]
Doi et al.

[11] Patent Number: 5,514,184
[45] Date of Patent: May 7, 1996

[54] ARTIFICIAL JOINT HAVING POROUS PORTION

[75] Inventors: Kenji Doi; Yoshio Sasaki; Hiroki Koga, all of Kobe, Japan

[73] Assignee: Kabushiki Kaisha Kobe Seiko Sho, Kobe, Japan

[21] Appl. No.: 249,627

[22] Filed: May 26, 1994

[30] Foreign Application Priority Data

May 26, 1993 [JP] Japan ..................................... 5-124174

[51] Int. Cl.[6] .................................. A61F 2/36; A61F 2/34
[52] U.S. Cl. ............................................... 623/23; 623/22
[58] Field of Search .................................. 623/23, 20, 18, 623/22, 16

[56] References Cited

U.S. PATENT DOCUMENTS

| | | | |
|---|---|---|---|
| 4,179,485 | 12/1979 | Tritten | 264/44 |
| 4,813,959 | 3/1989 | Cremascoli | 623/22 |
| 5,002,580 | 3/1991 | Noble et al. | 623/23 |
| 5,108,432 | 4/1992 | Gustavson | 623/16 |

*Primary Examiner*—David H. Willse
*Attorney, Agent, or Firm*—Oblon, Spivak, McClelland, Maier & Neustadt

[57] ABSTRACT

A total hip replacement type artificial joint comprising a stem and a socket, the stem being provided with a head at the upper end thereof and comprising a porous portion as an upper portion, a protector located under and along the porous portion and at the same height as the porous surface of the porous portion, an intermediate portion which underlies the porous portion and which is trapezoidal in section, and a lower portion which underlies the intermediate portion and which is circular in section, and the socket comprising an outer cup and a protector, the protector being provided along the outer peripheral edge of the outer cup and at the same height as a porous surface formed on the outer surface of the outer cup.

2 Claims, 4 Drawing Sheets

111
ARTIFICIAL JOINT HAVING POROUS PORTION

BACKGROUND OF THE INVENTION

1. Field of the Invention

The present invention relates to an artificial joint to be implanted into a human body after resection of an abnormal part in the case where the abnormal part is found in a bone such as the hip joint or the knee joint of the human body.

2. Description of the Related Art

For example, as to the hip joint, as shown in FIG. 4, a total hip replacement type prosthesis comprises a stem 1 and a socket 16, the stem 1 having a head 10 at the upper end thereof. When this prosthesis is implanted into the body of a patient, the stem 1 is embedded in intramedulla of femur 14 side, while the socket 16 on a pelvis 17 side. In many cases, the socket 16 comprises an outer cup (metal back) 2 which comes into contact with a living body bone and an inner cup 11 formed of a high density polyethylene and serving as a rotative slide surface with respect to the head 10. The outer cup 2 embedded in the pelvis 17 is fixed to the acetabulum with screws 12. As long as there does not occur any trouble, the stem and the socket remain embedded in the living body for a long period or during existence of the patient. For their replacement, a large-scale surgical operation is needed. Therefore, it is desirable that there occur no trouble after an initial operation.

According to the present stage of technical level, however, a limit is encountered in the duration of normal function of an artificial joint because it is the artificial joint that is embedded in the living body. There are a very large number of cases where even if the artificial joint exhibits its normal function just after the operation for embedding thereof, a trouble occurs with the lapse of 15 to 20 years. Of course, there are not a few cases where a trouble occurs in a shorter period due to some trouble of the artificial joint itself or due to a poor operation technique.

One serious trouble with the artificial hip joint or knee joint is loosening. This is a phenomenon such that the connection between a prosthesis and a living body bone becomes loose upon lapse of a certain period after a surgical operation. Once this phenomenon occurs, the patient will suffer pain, and there will occur wobbling of the joint to the extent that the artificial joint can no longer stand use.

For preventing the occurrence of such loosening over as long a period as possible after the surgical operation, it is important to improve the operation technique and make an appropriate design of the artificial joint itself. Although various improvements have been made and ample care exercised on the design of the artificial joint, it is the actual situation that the loosening phenomenon often occurs in a shorter period than expected. Therefore, the development of prostheses, including an artificial hip joint, of a superior design is desired.

As an example, reference will be made below to the case where bone cement is not used in an operation.

For preventing the occurrence of loosening over a long period, it is necessary to satisfy many conditions. Although various countermeasures have been proposed, there still remain many problems.

According to a stem of a type without bone cement, as shown in FIGS. 5(a), 5(b) and 5(c), the surface of an upper portion of the stem, indicated at 3, is made porous in order to improve the bonding between a bone of a living body and the stem. This porous portion, indicated at 3, is slightly higher than the base surface which is not porous to improve its contact with the living body bone. Also, the whole surface of an outer cup is made porous, as shown in FIGS. 6(a) and 6(b).

When these stem and outer cup are implanted into a living body, they are each driven forcibly into a slightly tight hole for ensuring a stronger contact with the associated bone. At this time, the particles in the porous surface may drop out partially. Such dropped-out particles staying within the bone can cause bone resorption or loosening.

On the other hand, when the patient's weight is imposed on the artificial hip joint after the surgical operation, the stem becomes easier to rotate, and this is presumed to be a cause of loosening. Therefore, it is desired to design an appropriate stem shape, taking into account by which portion of the stem the patient's weight is to be borne and the rotation is to be prevented and which portions of the stem are to resist varus or valgus deformity and bending.

SUMMARY OF THE INVENTION

The present invention has been accomplished for solving the above-mentioned problems and it is the object of the invention to provide an artificial joint wherein as to a stem, a protector is provided under a porous portion and at the same height as the porous surface, with the sectional shape being changed in the longitudinal direction of the stem, while as to an outer cup, a protector is provided along the peripheral edge of the outer cup and at the same height as a porous surface of the cup, to thereby prevent drop-out of the particles from the porous surfaces at the time of insertion into bones of a living body and permit the joint to bear the patient's weight imposed thereon after an operation.

In the first aspect of the present invention there is provided an artificial joint including a stem, the stem comprising a porous portion as an upper portion, a protector located under and along the porous portion and at the same height as the porous surface, an intermediate portion which underlies the porous portion and which is trapezoidal in section, and a lower portion which underlies the intermediate portion and which is circular in section.

In the second aspect of the present invention there is provided an artificial joint including a socket, the socket comprising an outer cup and a protector, the protector being provided along the outer peripheral edge of the outer cup and at the same height as a porous surface formed on the outer surface of the cup.

In the third aspect of the present invention there is provided a total hip replacement type artificial joint comprising a stem and a socket which stem is provided with a bone head at the upper end thereof.

The porous portion of the stem is slightly higher than the stem base surface in order to improve its contact with a bone of a living body when inserted into intramedulla of femur. There has been a fear of dropout of the surface particles of the porous portion upon insertion of the stem into a bone of a living body and upon striking of the porous portion against the bone. However, this fear can be eliminated by providing a protector under and along the porous portion at the same height as the porous surface. When the stem is inserted into the living body bone, the protector is the first to strike against the bone, so that there no longer occurs drop-out of particles from the porous surface.

Further, since the sectional shape of the stem is varied in its longitudinal direction, that is, the intermediate portion which underlies the porous portion is trapezoidal in section and the lower portion which underlies the intermediate portion is circular in section, there can be ensured resistance of the stem to rotation, varus or valgus deformity and bending when the patient's weight is imposed on the artificial hip joint after an operation.

Thus, the porous portion takes charge of bearing the patient's weight. The bone of the living body grows and enters the porous portion and exhibits a strong supporting force as integrally with the porous portion. In the portion of a trapezoidal section which underlies the porous portion, as shown in FIG. 3, four corners 9 of a trapezoid are in direct touch with a cortical bone 15 of femur 14 to resist rotation of the stem 1. The portion of a circular section which underlies the trapezoidal section is straight and its surface is finished as a mirror surface. In this way the stem is shaped to resist its varus or valgus deformity and bending, not expecting integration with the living body bone.

On the socket outer cup side, a protector is provided along the peripheral edge of the cup and at the same height as the porous surface of the cup. This portion exhibits the greatest rubbing force (shear force) with the bone when the outer cup is inserted into the acetabulum. In the presence of such a protector there no longer occurs drop-out of particles from the porous surface of the outer cup upon insertion of the cup into the bone.

Thus, the artificial joint of the present invention and the total hip replacement type artificial joint including the same can bear the patient's weight after a surgical operation without drop-out of particles from the porous surface when inserted into a bone of a living body.

DETAILED DESCRIPTION OF THE PREFERRED EMBODIMENT

An embodiment of an artificial joint according to the present invention will be described below.

Figure 1:
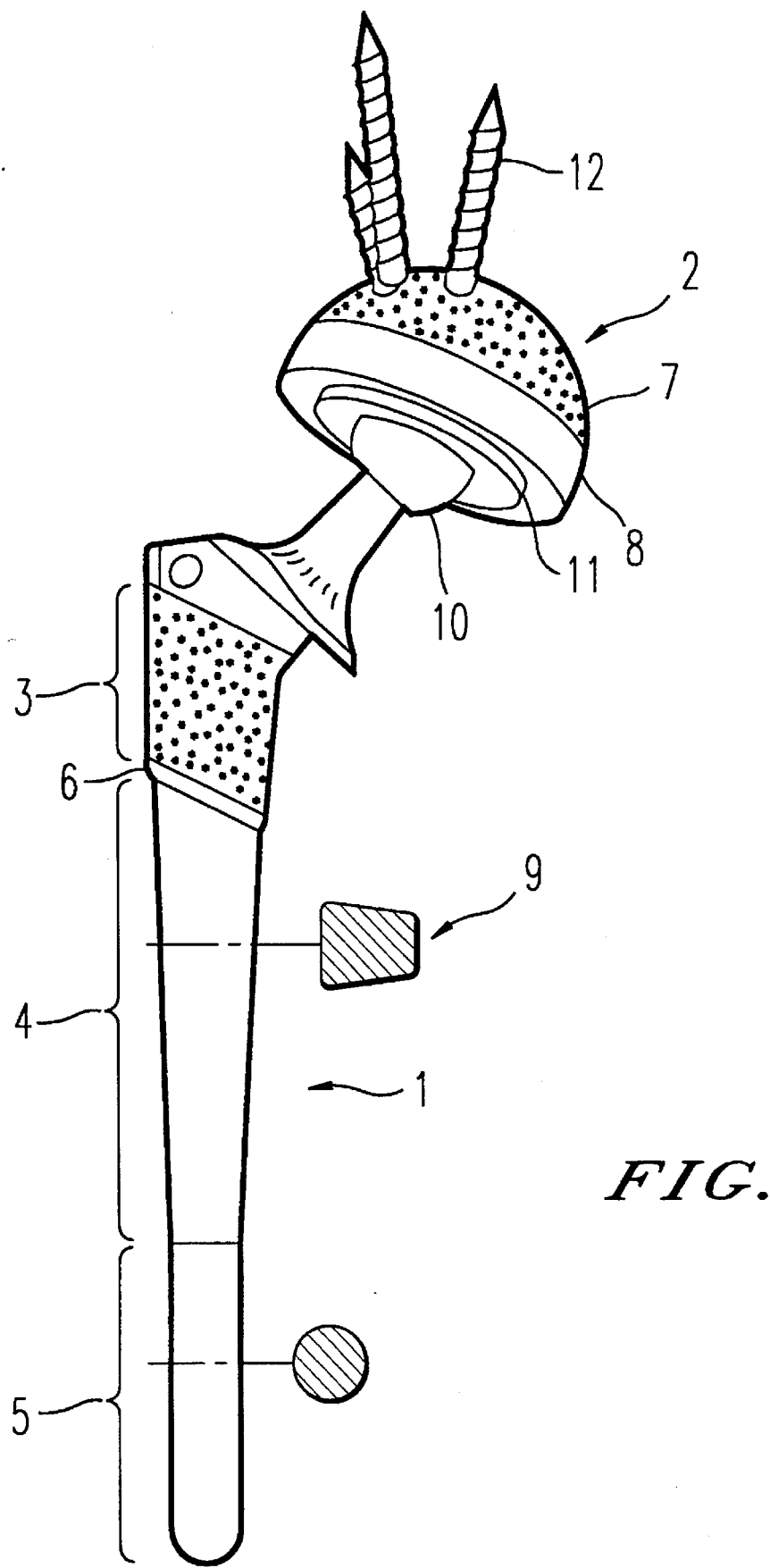
FIG. 1 is a view showing an assembled state of a total hip replacement type artificial hip joint according to the present invention.
Figure 2:
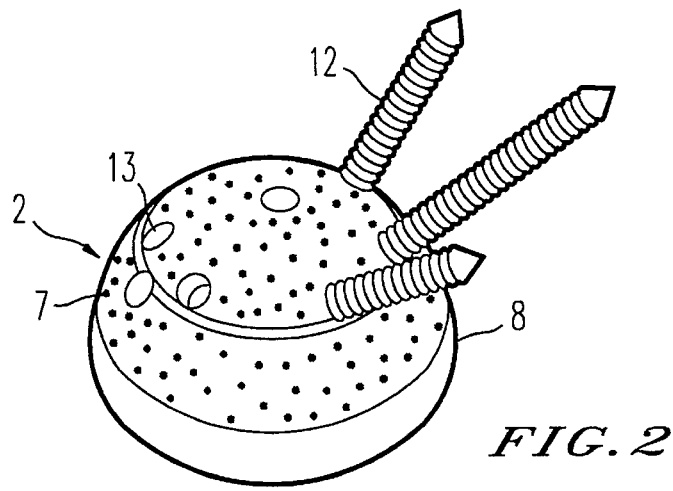
FIG. 2 is a view showing an outer cup of a socket used in the artificial hip joint.
Figure 3:
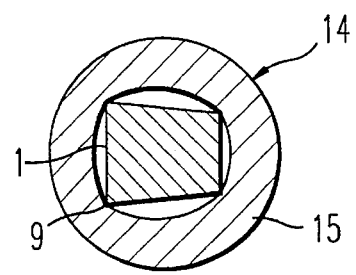
FIG. 3 is a view showing a relation between the corners of a trapezoidal portion which underlies a porous portion in a stem of the artificial joint and a cortical bone of the femur.
Figure 4:
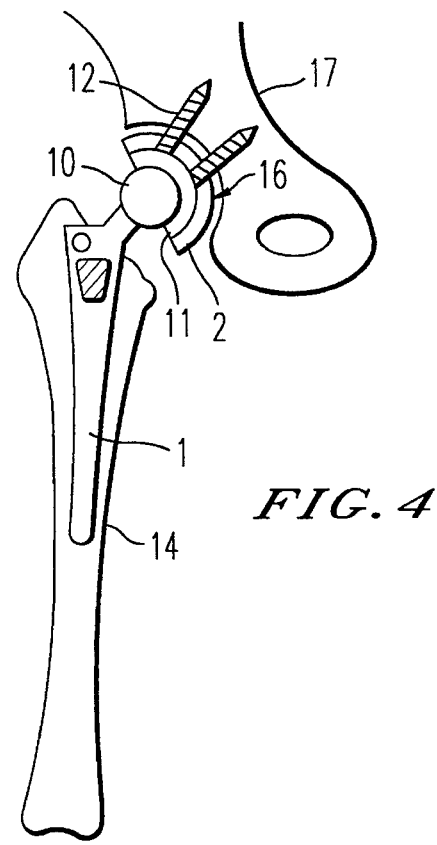
FIG. 4 is an explanatory view of an artificial hip joint.
Figure 5C:
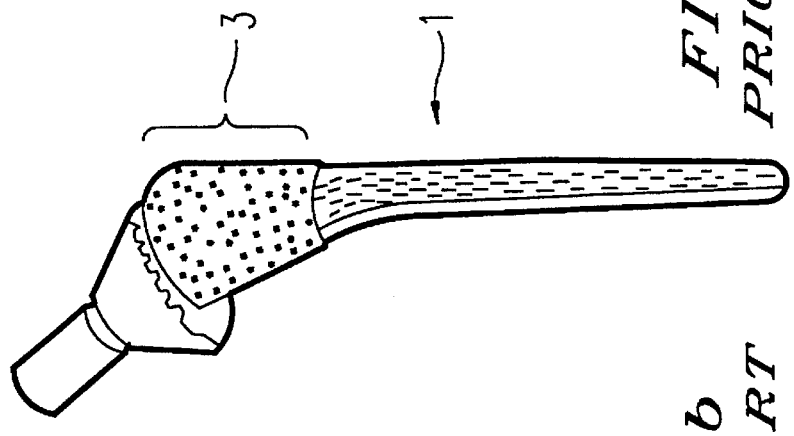
FIGS. 5(a) to 5(c) are views showing an example of a conventional stem shape.
Figure 5B:
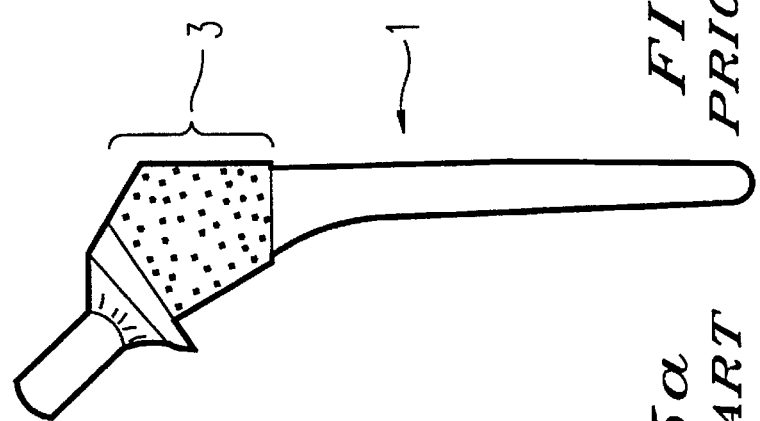
Figure 5A:
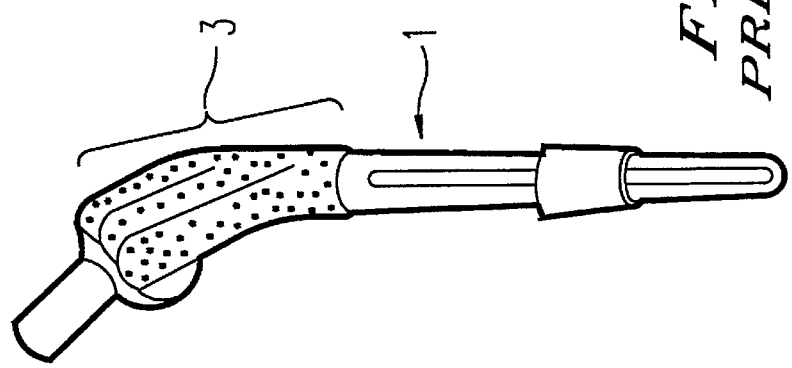
Figure 6B:
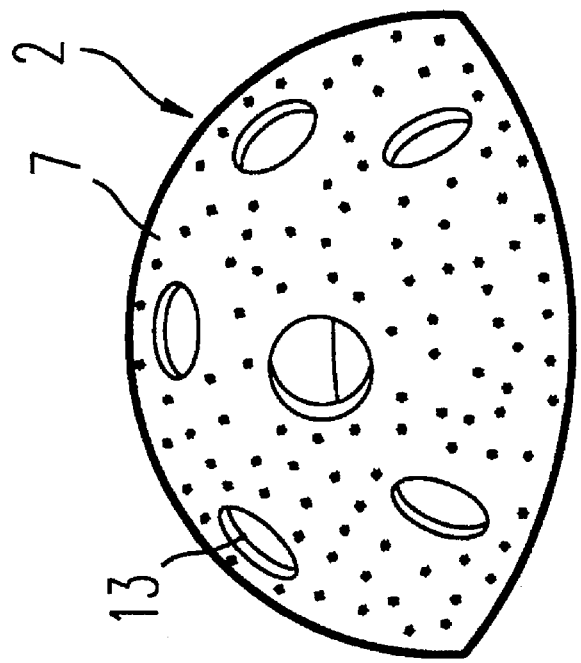
FIGS. 6(a) and 6(b) are views showing an example of a conventional outer cup shape.
Figure 6A:
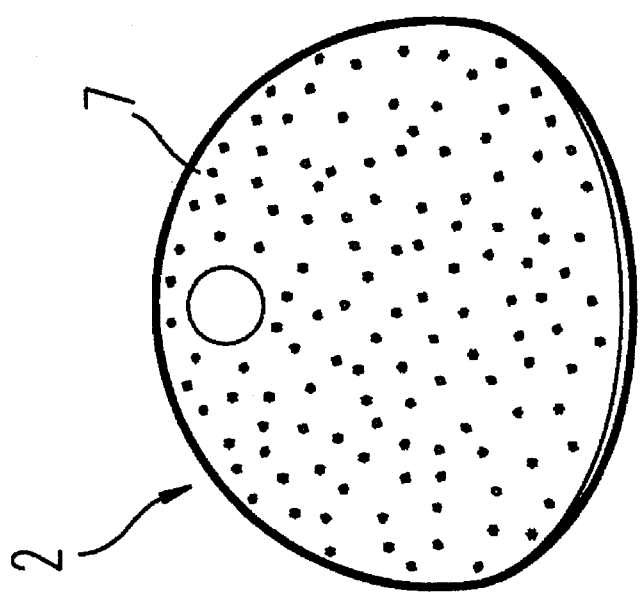

FIG. 1 illustrates an assembled state of a total hip replacement type artificial hip joint and FIG. 2 illustrates an outer cup of a socket. In these figures, the reference numeral 1 denotes a stem, which comprises a porous portion 3 as a proximal portion, a trapezoidal portion 4 as an intermediate portion and a circular portion 5 as a distal portion. Under the porous portion 3 is provided a protector 6 which is finished to the same height as the porous surface of the porous portion 3. A head 10 is provided at the upper end of the stem 1, and an inner cup 11 and an outer cup 2 of a socket are provided so as to cover the head 10. Further, a protector 8 is provided along the peripheral edge of the outer cup 2 and at the same height as a porous surface 7 of the outer cup. The outer cup 2 has holes 13 formed for insertion therein of screws 12 to fix the outer cup to the pelvis after insertion of the cup.

When the artificial hip joint is inserted into bones of a living body, the drop-out of particles from the porous surface which may occur at the time of insertion of the stem into the femur can be prevented by the protector 6. Likewise, the fear of such drop-out at the time of insertion of the outer cup 2 into the acetabulum can be eliminated by the protector 8.

The porous portion 3 acts to support the patient's weight because the living body bone grows and enters the porous portion after a surgical operation and exhibits a strong supporting force integrally with the porous portion. The trapezoidal portion 4 as an intermediate portion is finished in a trapezoidal shape in section and its four corners 9 come into direct touch with the cortical bone in the femur to provide resistance to the rotation of the stem 1 upon imposition of the patient's weight on the stem after an operation. The circular portion 5 as a distal portion is circular in section and is finished straight so as to have a mirror surface; it provides resistance to varus or valgus deformity and bending of the stem 1 upon exertion of the patient's weight on the stem after a surgical operation, without expecting integration with the associated bone of the living body.

Although in the above embodiment reference was made to the artificial hip joint, the same effects as above can be attained also in the case of an artificial knee joint. Additionally, the present invention is applicable also to other artificial bones if only the method of insertion into the bones is the same as above.

As set forth above, the artificial joint and total hip replacement type artificial joint according to the present invention can prevent drop-out of particles from the porous surfaces and can bear the patient's weight imposed thereon after a surgical operation, thus being employable within the patient's body over a long period without the occurrence of loosening. Thus, they are extremely useful.

What is claimed is:

1. An artificial joint comprising:

an elongate stem having opposite first and second ends along a direction of elongation of said stem, said stem generally tapering from said first end toward said second end; and another element movably cooperating with said first end of said stem to form a joint therebetween, wherein said stem further comprises:

a porous portion having, in a section transverse to a longitudinal axis of said stem, a porous surface, an intermediate portion having a trapezoidal shape with four corners, said intermediate portion being located closer to said second end relative to said porous portion and having a smaller radial size than said porous surface, a protector portion positioned adjacent said porous portion and between said porous portion and said intermediate portion, said protector portion having a radial size greater than that of the intermediate portion and corresponding to that of the adjacent porous portion, and a lower portion having a circular section and located closer to said second end relative to said porous portion.

2. The artificial joint of claim 1 wherein said other element comprises a socket part.

* * * * *